United States Patent [19]

Sakai et al.

[11] Patent Number: 4,973,163
[45] Date of Patent: Nov. 27, 1990

[54] METHOD FOR MEASURING BIREFRINGENCE

[75] Inventors: Kiyokazu Sakai, Nishinomiya; Shigeyoshi Osaki, Takarazuka, both of Japan

[73] Assignee: Kanzaki Paper Manufacturing Co., Ltd., Japan

[21] Appl. No.: 417,177

[22] Filed: Oct. 4, 1989

[30] Foreign Application Priority Data

Oct. 8, 1988 [JP] Japan ................. 63-254483
Oct. 8, 1988 [JP] Japan ................. 63-254484

[51] Int. Cl.$^5$ .................. G02F 1/01; G01B 11/18
[52] U.S. Cl. ................... 356/367; 250/225; 356/35
[58] Field of Search ........... 356/366, 367, 368, 370, 356/33, 34, 35; 250/225

[56] References Cited

U.S. PATENT DOCUMENTS

| | | | |
|---|---|---|---|
| 3,177,761 | 4/1965 | Redner | 356/366 |
| 3,376,652 | 3/1968 | Flader | 356/33 |
| 4,554,449 | 11/1985 | Taniudri et al. | 250/225 |
| 4,849,623 | 7/1989 | Osaki et al. | 356/368 |

FOREIGN PATENT DOCUMENTS 1402857  6/1988  U.S.S.R. .................. 356/366

*Primary Examiner*—Richard A. Rosenberger
*Attorney, Agent, or Firm*—Lowe, Price, LeBlanc, Becker & Shur

[57] ABSTRACT

The combination of a polarizer and an analyzer, and a sample interposed therebetween are rotated relative to each other to determine the relationship between the angle of rotation and the intensity of light transmitted through the arrangement. The birefringence of the sample is obtained from the retardation values calculated from the result of the determination. When the determination is made for two kinds of light with different wavelengths close to each other, the retardation can be determined straightforwardly. When at least three kinds of light with different wavelengths are used for the determination, different retardation values are obtained for the respective wavelengths for a highly accurate analysis.

4 Claims, 3 Drawing Sheets

①: fluorinated polymer (148 μm thick)
②: Polyethylene terephthalate (58 μm thick)
③: polystyrene (60 μm thick)
④: polyethylene terephthalate (15 μm thick)
⑤: polyethylene terephthalate (44 μm thick)
⑥: polypropylene (59 μm thick)

METHOD FOR MEASURING BIREFRINGENCE

FIELD OF INDUSTRIAL APPLICATION

The present invention relates to a method for determining the birefringence of various materials based on optical measurements.

PRIOR ART

In optical devices, the birefringence of optical materials not infrequently poses problems, for example, in respect of accuracy of measurements. Plastics sheets and the like are given double refractive properties when drawn, so that the degree of orientation due to drawing or extension is detectable from the birefringence for quality control. Thus, there arises a need to measure the birefringence of materials in various cases, whereas the use of Abbe's refractometer involves limitations to the shape of samples, requires a cumbersome measuring procedure and encounters difficulties in displaying the result of measurement straightforwardly. As another method, birefringence may be measured by placing the sample between a polarizer and an analyzer intersecting the polarizer at right angles therewith, causing white light to irradiate on the arrangement, and determining the retardation of the sample (difference between the optical path lengths for normal light and abnormal light through the sample) from the interference color of the transmitted light with reference to an interference color diagram. However, this method is experimental, low in accuracy and difficult to practice automatically since the color must be identified. Accordingly, methods of measuring birefringence accurately and automatically are proposed in Unexamined Japanese Patent Publications SHO 60-13245 and SHO 52-65489, etc. With these methods, linearly polarized light of a single wavelength is caused to impinge on the sample, and the ratardation of the sample is determined from the state of rotary polarized light through the sample. With respect to the direction of polarization of polarized light incident on samples perpendicular to the plane thereof, the sample which permits double refraction has a direction in which the sample has a maximum refractive index and a direction, perpendicular to the above direction, in which the sample exhibits a minimum refractive index. Suppose the maximum refractive index and the minimum refractive index, which are termed main refractive indexes, are $n1$ and $n2$, respectively, and the thickness of the sample is $T$. The retardation $Rt$ is then given by $T(n1-n1)$. Nevertheless, the value directly given by the proposed methods is not $Rt$ or $(n1-n2)$ but a fraction obtained by dividing $Rt$ by the wavelength, i.e., a fraction corresponding to the phase difference between the normal light transmitted by the sample and abnormal light therethrough. For varying $Rt$ values, the phase difference merely varies periodically from 0 to $2\pi$, so that it is impossible to determine $Rt$ straightforwardly. With the foregoing publication SHO 60-13245, $Rt$ is determined from $T$ which is calculated from the attenuation of transmitted light using the absorption coefficient of the sample. On the other hand, the method of the publication SHO 62-65489 is employed only for thin samples with a retardation value generally of not greater than one-half the wavelength.

The main object of the present invention is to provide a method for accurately determining the birefringence of samples by a simple procedure free of limitations to the thickness of the sample.

SUMMARY OF THE INVENTION

To fulfil the above object, the present invention provides a method for measuring the birefringence of a sample characterized by inserting the sample between a polarizer and an analyzer in combination therewith, the polarizer and the analyzer having their directions of polarization fixed at a specified angle with each other, determining the relationship between the angle of rotation and the intensity of light transmitted through the polarizer, the sample and the analyzer when the polarizer and the analyzer are rotated relative to the sample, for two kinds of light which are close to each other in wavelength so as to exhibit substantially the same refractive index, selecting a pair of values closest to each other respectively from a multiplicity of retardation values calculated from the result of the determination for the light of one of the wavelengths and from a multiplicity of retardation values calculated from the result of the determination for the light of the other wavelength, and calculating the birefringence from the selected values.

When retardation is calculated with light of a particular wavelength, numerous calculated retardation values are obtained for a specific phase difference of the light emanating from the sample.

On the other hand, when two kinds of light with different wavelengths are used for measurement, the most suitable retardation value $Rt$ can be determined from numerous calculated retardation values in the following manner. First, two kinds of light are selected which are suitably close to each other in wavelength because if two kinds of light which differ greatly in wavelength are used, the difference in refractive index due to the wavelength difference influences the measurements. Accordingly, the two kinds of light to be selected are close to each other in wavelength so that they can be regarded as substantially identical in refractive index. Owing to the difference in wavelength, in this case, the two kinds of light differ in the number of waves within the sample when the light passes through the sample and are consequently different in the sequence of numerous calculated retardation values obtained. However, in the case of two kinds of light which are so close in wavelength that they can be regarded as substantially identical in refractive index, they are to be substantially identical also in retardation value. It is therefore possible to find values most approximate to each other from the two sequences of retardation values obtained by calculation and to thereby determine a suitable retardation value $Rt$ straightforwardly. Thus, the birefringence $(n1-n2)$ can be obtained by substituting $Rt$ and known $T$ in the above equation $Rt = T(n1-n2)$.

Next, in the case where at least three kinds of light with different wavelengths are used for the measurement, a more accurate retardation value can be obtained with the difference in refractive index due to wavelength considered as will be described in detail with reference to the embodiment to follow. This can be accomplished by (i) performing the same measurement and calculation as described above for the three or more kinds of light to obtain at least three kinds of calculated retardation values each as a function of the wavelength concerned, (ii) applying Cauchy' formula established between the refractive index and the wavelength of visible light to the functions of at least three kinds of retardation values to obtain sequences (distribution curves) of retardation values for the light of different wavelengths, and (iii) finding a set of values most approximate to one another from these sequences. Since variations in retardation value are small relative to variations in wavelength, the different kinds of light with varying wavelengths are close to one another in retardation value. Accordingly, the set of values affords a proper retardation value at a particular wavelength.

Neither of the methods described above involve any limitation to the thickness of samples, nor do they require a method, such as discrimination of a particular color, producing a result that will differ from person to person. Thus, the birefringence of samples can be determined by these methods easily and accurately.

Especially when two kinds of light are used which are different from but close to each other in wavelength, birefringence can be determined with great ease.

The present invention also provides a method for measuring the birefringence of a sample characterized by inserting the sample between a polarizer and an analyzer in combination therewith, the polarizer and the analyzer having their directions of polarization fixed at a specified angle with each other, determining the relationship between the angle of rotation and the intensity of light transmitted through the polarizer, the sample and the analyzer when the polarizer and the analyzer are rotated relative to the sample, for at least three kinds of light, selecting a set of values closest to one another from a multiplicity of retardation values calculated from the result of the determination for the light of each wavelength, determining a retardation value for each wavelength, and calculating the birefringence for each wavelength from the resulting value. In the case where at least three kinds of light are used which differ from one another in wavelength, the birefringence can be determined for each wavelength. Generally, variations in birefringence are very small relative to variations in wavelength, such that the main refractive indexes directly measured by conventional Abbe's refractometer are low in accuracy and are not useful. The methods of the invention described above are free of this problem and provide many items of data for checking materials for characteristics and for the quality control in working processes, etc. utilizing the dependence of the birefringence on wavelength.

Other objects and advantages of the present invention will become apparent form the following description of embodiments with reference to the accompanying drawings.

EMBODIMENTS

Figure 1:
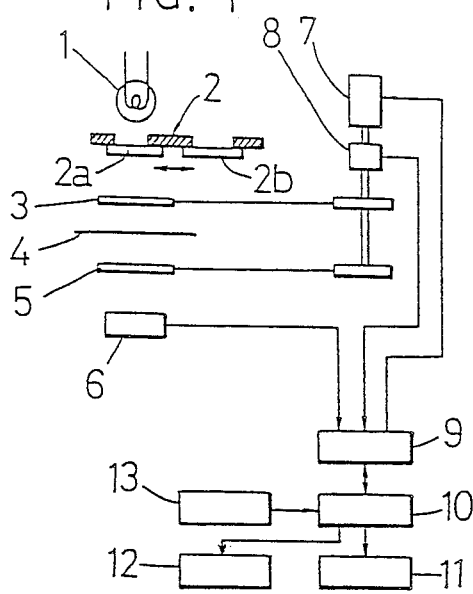
FIG. 1 is a block diagram showing a device for practicing the method of the invention.

FIG. 1 shows an embodiment of the invention which comprises a light source 1 and a filter plate 2 having changeably attached thereto two monochromatic filters 2a and 2b each for passing light of a single wavelength therethrough. These filters differ from each other in the wavelength of light passing therethrough, such that one of two kinds of light, λ1 and λ2 in wavelength, is available from the light source 1 selectively. A polarizer 3 and an analyzer 5 are rotatable together by a motor 7 with their directions of polarization maintained at a specified angle with each other, e.g., in parallel to each other in the present embodiment. Indicated at 4 is a sample interposed between the polarizer 3 and the analyzer 5, and at 6 a photodetector for receiving the light through the anaylizer 5 to produce a signal in accordance with the intensity of the light. A computer 10 receives through an interface 9 the output signal from the photodetector 6 and an output signal from a rotation angle sensor 8 attached to the motor shaft for data processing and controlling the motor 7. The result of data processing by the computer 10 is displayed on a CRT 11 and recorded by a printer 12. A keyboard 13 is used for giving the computer 10 various commands and parameters required for data processing.

Figure 2:
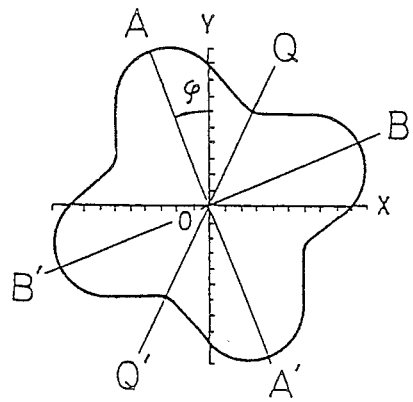
FIG. 2 is a graph showing the result of measurement obtained at a wavelength.
Figure 3:
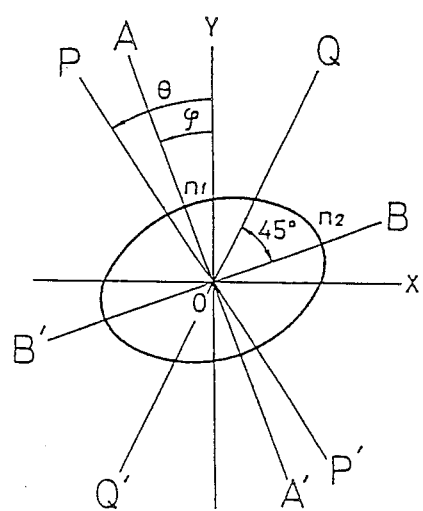
FIG. 3 is a diagram for illustrating angles, directions, etc. for use in the description of the present method.

FIG. 2 is a graph obtained from an output of the device wherein the filter 2a is selected with a sample placed at the illustrated position, by expressing the output on a polar coordinate system as a function $\phi$ of the angle of rotation of the polarizer 3 and the analyzer 5 rotatable together. When linearly polarized light is incident on the sample which has birefringence, the light transmitted through the sample is generally elliptically polarized light, and the ratio between the major axis and the minor axis thereof and the direction of the major axis vary with the thickness of the sample. FIG. 3 shows the indicatrix of the sample, in which X-axis and Y-axis are coordinate axes on a plane perpendicular to the optical Z-axis of the device. The angle of rotation 8 of the polarizer and the analyzer is expressed with respect to Y-axis. In FIG. 3, n1 and n2 are two main refractive indexes, AA' and BB' are the directions of the respective main refractive indexes n1, n2, and PP' are the direction of polarization of the polarizer and the analyzer. When the direction of polarization PP' coincides with AA' or BB', no double refration occurs. Since the incident light then passes through the sample and the analyzer as it is, the output of the photodetector is maximal in the directions AA' and BB' as will be understood from FIG. 2. When the direction of polarization PP' is a direction QQ' which is intermediate between the directions AA' and BB' and at 45° with the directions AA' and BB', the component in the direction AA' and the component in the direction BB' of the linearly polarized light incident on the sample are equal to each other in amplitude, and the amplitude is $1\sqrt{2}$ of the amplitude of the incident light, A. When the component in the direction AA' matches the component in the direction BB' in phase when passing through the sample, the emergent light becomes linearly polarized light in the direction QQ' which is equal to the incident light in amplitude, and the output of the photodetector is the same as that obtained when the direction of polarization of the polarizer and the analyzer is the direction AA' or BB'. If the phase difference between the components of the light transmitted through the sample in the two directions of main refractive indexes is 90° when the direction of polarization, PP', is the direction QQ', the transmitted light is circularly polarized light with an amplitude of $A/\sqrt{2}$, and the intensity of light detected is ½ of the maximum. When the phase difference is 180°, the transmitted light is linearly polarized in a direction perpendicular to the direction of the polarized light obtained when the phase difference is 0 and is prevented by the analyzer to give a light detection signal of 0. Thus, the phase difference involved in the transmitted light in the two directions of the main refractive indexes can be known from the ratio of the light detection signal value in the direction at an angle of 45° with the direction in which the maximal value is obtained in FIG. 2 to the maximum value of the light detection signal.

Now, the two main refractive indexes n1, n2 to be determined from the phase difference involved in the transmitted light will be considered. Since there are two unknowns, the two main refractive indexes can not be determined if the data as to the phase difference is a single item. Accordingly, the second filter 2b is selected to perform the same measurement as above. When the direction of polarization of the polarizer and the analyzer is the direction QQ', the phase difference between the components in the two directions of main refractive indexes of the sample transmitted light differs from the value obtained with the filter 2a. Using the filters 2a, 2b, two kinds of light with wavelengths λ1, λ2 are selected which are so close to each other in wavelength that they can be regarded as substantially identical in main refractive indexes. It is then possible to determine the two main refractive indexes n1 and n2 in the following manner.

Assuming that the thickness of the sample is T, the number of waves, N1, of light with the wavelength λ1 within the sample at the refractive index n1 is given by $$T_i \; N1 = n1 \times T/\lambda 1$$

Similarly, the number of waves, N2, at the refractive index n2 is given by $$N2 = n2 \times T/\lambda 1$$

When polarized light with the wavelength λ1 is incident on the sample, the phase difference Δ1 involved in the light emanating from the sample in the two $$\Delta 1 = 2\pi(N1 - N2) = \frac{2\pi}{\lambda 1} T(n1 - n2)$$

When the direction of polarization of the polarizer and the analyzer is the direction QQ' in FIG. 3, the components of the incident light in the two directions of main refractive indexes have the same phase and the same amplitude, so that the amplitude of the emanating light with the phase difference of Δ1 can be determined by the following method.

First, a case will be considered in which the absorption coefficient of the sample is not different with the direction of polarization. When the light incident on the sample is linearly polarized light in the direction QQ' and has an amplitude of A, the amplitude of the component in the direction of main refractive index n1 is $A/\sqrt{2}$, and the amplitude of the component thereof in the direction QQ' is A/2. When the amplitude of this component is expressed as $(A/2)\cos \omega t$, the component in the direction QQ' of the component in the direction of main refractive index n2 is expressed by $$(A/2)\cos(\omega t - \Delta 1)$$

since the component is delayed by Δ1 in phase. When the former is expressed as $(A/2)\cos(\omega t + \Delta 1/2)$ for the convenience of calculation, the latter can be expressed as $(A/2)\cos(\omega t - \Delta 1/2)$. Accordingly, the amplitude of the component in the direction QQ' of the light emanating from the sample is given by $$\frac{A}{2} \left\{ \cos\left(\omega t + \frac{\Delta 1}{2}\right) + \cos\left(\omega t - \frac{\Delta 1}{2}\right) \right\} \quad (a)$$

This can be simplified as $$A\cos\frac{\Delta 1}{2} \cos\omega t \quad (b)$$

The amplitude Aq of the component in the direction QQ' of the light emanating from the sample is $$Aq = A\cos\frac{\Delta 1}{2}$$

Accordingly, the output of the photodetector is $$A^2 q = A^2 \cos^2 \frac{\Delta 1}{2}$$

Since the maximum of the photodetector output is detected as A when the direction of polarization of the polarizer and the analyzer is the direction AA' or BB', the ratio of maximum to minimum $Aq^2/A^2$, i.e., R1, is $$R1 = \cos^2 \frac{\Delta 1}{2} = \cos^2 \frac{\pi}{\lambda 1} T(n1 - n2) \quad (1)$$

Similarly when light with the wavelength λ2 is used for measurement, the ratio is $$R2 = \cos^2 \frac{\pi}{\lambda 2} T(n1 - n2) \quad (2)$$

which is obtained by changing the adscript in the above equation to 2.

In the above equations (1) and (2), R1 and R2 are measurements, and Δ1, Δ2 and the thickness T of the sample are known, so that n1 and n2 can be calculated from the equations (1) and (2).

In actuality, it is generally desired to merely obtain the retardation value T(n1−n2), so that the following equation is obtained from the equation (1).

$$\cos^{-1}\sqrt{R1} = \frac{\pi}{\lambda 1} T(n1 - n2) \quad (3)$$

There are numerous values for T(n1−n2) which satisfy the equation (3). Similarly, the equation (2) gives the following equation.

$$\cos^{-1}\sqrt{R2} = \frac{\pi}{\lambda 2} T(n1 - n2) \quad (4)$$

There are numerous values for T(N1−n2) which satisfy the equation (4). Since both the equations (3) and (4) are established at the same time, a suitable retardation value can be obtained straightforwardly by averaging a set of values which are closest to each other and selected from suitable ranges of numerous retardation values in the respective sequences. (Theoretically there are values which are perfectly in agreement, whereas such values are not available actually owing to measurement errors.)

The method described above is used in the case where the absorption coefficient of the sample does not vary with the direction of polarization. When the absorption coefficient differs relative to polarization in the directions of main refractive indexes n1 and n2, the ratio of the absorption coefficient a1 to the absorption coefficient a2, i.e., a1/a2, is assumed to be α. In this case, the absorption coefficient ratio is dependent on the photodetector output ratio when the direction of polarization of the polarizer and the analyzer is the directions AA' and BB' and the square root thereof is assumed to be α. From the equation (a) we obtain $$\frac{A}{2}\left(\cos\left(\omega t + \frac{\Delta 1}{2}\right) + \alpha\cos\left(\omega t - \frac{\Delta 1}{2}\right)\right)$$

From the equation (b) we obtain $$\frac{A}{2}\left\{(1+\alpha)\cos\frac{\Delta 1}{2}\cos\omega t + (1-\alpha)\sin\frac{\Delta 1}{2}\sin\omega t\right\}$$

This expression becomes $$\frac{A}{2}\sqrt{1+\alpha^2+2\alpha\left(\cos^2\frac{\Delta 1}{2}-\sin^2\frac{\Delta 1}{2}\right)}\cos(\omega t + \chi)$$

The above expression can be simplified as $$\frac{A}{2}\sqrt{1+\alpha^2+2\alpha\cos\Delta 1}\cos(\omega t + \chi)$$

Therefore from the equations (1), (2) we obtain $$R1 = \frac{1}{4}\left\{1+\alpha 1^2 + 2\alpha 1\cos\frac{2\pi}{\lambda 1}T(n1-n2)\right\} \tag{5}$$

$$R2 = \frac{1}{4}\left\{1+\alpha 2^2 + 2\alpha 2\cos\frac{2\pi}{\lambda 2}T(n1-n2)\right\} \tag{6}$$

The values R1, R2, α1 and α2 in the equations (5) and (6) are actual measurements, so that T(n1—n2) can be determined in the same manner as above. Each of R1 and R2 used is the ratio of the photodetector output in the direction of the main refractive index n1, i.e., the direction AA' in FIG. 3, to the photodetector output in the direction QQ', because the above calculations are based on these directions.

The method of the invention was compared with the method wherein retardation is measured by using a compensator. Table 1 shows the results obtained for six samples (i) by determining the retardation of the sample from an observation of interference color using a polarization microscope and Berek compensator, and (ii) by measuring retardation values by the method of the invention using light with wavelengths of λ1=590.0 nm and λ 2=657.3 nm and determining a set of Rt values with a minimum difference therebetween, from the respective sequences of retardation values in the range of less than 300 nm.

The six samples used were PET (polyethylene terephthalate; 58/μm), FEP (fluorinated polymer; 148/μm), PS (polystyrene; 48/μm), PP (polypropylene; 28/μm), PS (polystyrene; 111/μm) and PP (polypropylene; 28/μm). The results of Table 1 show that the measurements obtained by the Berek compensator closely resemble to those obtained by the method of the invention and that retardation values not smaller than ½ of the measuring wavelength can be determined by the method of the invention. With respect to the accuracy of measurements, the use of the Berek compensator has the drawback that the error increases as Rt increases because of the characteristics thereof and that different measurers produce different values. On the other hand, when the Rt of a sample was measured by the present method 20 times successively, the standard deviation of Rt was up to 0.1 nm, hence high accuracy.

TABLE 1

| | | | Retardation value measured (nm) | | |
|---|---|---|---|---|---|
| | | Thickness of sample | With Berek compensator | Method of invention | |
| No. | Sample | (μm) | | λ = 590.0 nm | λ = 657.3 nm |
| 1 | PET | 58 | 51 | 50.8 | 48.4 |
| 2 | FEP | 148 | 102 | 102.4 | 101.2 |
| 3 | PS | 48 | 221 | 219.0 | 215.4 |
| 4 | PP | 28 | 431 | 417.6 | 417.7 |
| 5 | PS | 111 | 637 | 623.7 | 608.2 |
| 6 | PP | 28 | 804 | 791.7 | 790.4 |

Figure 4:
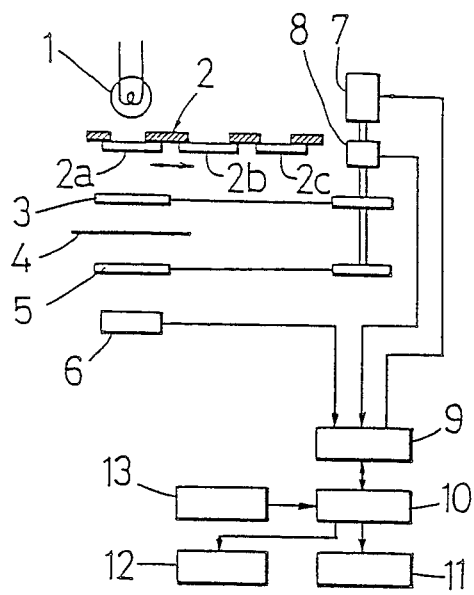
FIG. 4 is a block diagram showing another device for practicing the method of the invention.

FIG. 4 shows another embodiment of the invention wherein a filter plate 2 has replaceably attached thereto three monochromatic filters 2a, 2b and 2c which are different in the wavelength of light to be passed therethrough, and the light of one of three wavelengths λ 1, λ2 and λ3 form a light source 1 is made available selectively. With exception of this feature, the device is the same as the one shown in FIG. 1. Like parts are designated by like reference numerals. This device is used in the same manner as the device of FIG. 1.

Suppose the two main refractive indexes of the sample are n11 and n12 for the light of wavelength λ1, n21 and n22 for the light of wavelength λ2, and n31 and n32 for the light of wavelength λ3, and the thickness of the sample is T.

First, a case will be considered in which the light absorption coefficient of the sample does not differ with the direction of polarization. It is assumed that the light incident on the sample is lineally polarized light in the direction QQ' with an amplitude of A and that the component of light emanating from the sample in the direction QQ' has an amplitude of Aq. Based on the same concept as in the foregoing embodiment, the ratio between the maximum and the minimum of the photodetector output $Aq^2/A^2$, i.e., R1, is given by $$R1 = \cos^2\frac{\Delta 1}{2} = \cos^2\frac{\pi}{\lambda 1}T(n11-n12) \tag{11}$$

Similarly, the ratios R2 and R3 for the measurement with wavelengths λ2 and λ3 are expressed by $$R2 = \cos^2\frac{\pi}{\lambda 2}T(n21-n22) \tag{12}$$

$$R3 = \cos^2\frac{\pi}{\lambda 3}T(n31-n32) \tag{13}$$

which are obtained by changing the adscript in the equation (11) to 2 and 3, respectively. R1, R2 and R3 in the equations (11), (12) and (13) are measured values, and λ1, λ2 and λ3 and the thickness of the sample, T, are known, so that n11, n12, etc. can be calculated from the equations (11) to (13). In actuality, it is generally desired to merely obtain the retardation value T(n11-n12), so that the equation 11 affords the following equation.

$$\cos^{-1}\sqrt{R1} = \frac{\pi}{\lambda 1} T(n11 - n12) \quad (14)$$

There are numerous values of T(n11−n12) which satisfy the equation (14). Similarly, the equations (12) and (13) provide $$\cos^{-1}\sqrt{R2} = \frac{\pi}{\lambda 2} T(n21 - n22) \quad (15)$$

$$\cos^{-1}\sqrt{R3} = \frac{\pi}{\lambda 3} T(n31 - n32) \quad (16)$$

Numerous values of T(n21−n22) and T(n31−n32) are also present which satisfy the equations (15) and (16). Since the equations (14) to (16) are established at the same time, a set of values are obtained which are most approximate to one another and selected from the respective sequence of the numerous retardation values in a suitable range.

In the case where the absorption coefficient for the polarized light in the two directions of main refractive indexes is different, the ratio between the amplitude absorption coefficient a11 and a12 for the light of the wavelength λ1, etc. is assumed to be a11/a12=α1. In the same way, α2 and α3 are obtained on the basis of a21, a22 and a31, a32. In this case, the ratio of absorption coefficients is dependent on the ratio between the photodectector outputs when the direction of polarization of the polarizer and the analyzer is AA' and BB'. The square root of the ratio is assumed to be αi (i=1, 2, 3). The equation (a) is expressed by $$\frac{A}{2}\left\{\cos\left(\omega t + \frac{\Delta 1}{2}\right) + \alpha 1 \cos\left(\omega t - \frac{\Delta 1}{2}\right)\right\}$$

The equation (b) is expressed by $$\frac{A}{2}\left\{(1 + \alpha 1)\cos\frac{\Delta 1}{2}\cos\omega t + (1 - \alpha 1)\sin\frac{\Delta 1}{2}\sin\omega t\right\}$$

These expressions can be expressed by $$\frac{A}{2}\sqrt{1 + \alpha 1^2 + 2\alpha 1\left(\cos^2\frac{\Delta 1}{2} - \sin^2\frac{\Delta 1}{2}\right)\cos(\omega t + x)}$$

The expression is simplified as $$\frac{A}{2}\sqrt{1 + \alpha 1^2 + 2\alpha 1\cos\Delta 1\cos(\omega t + x)}$$

Accordingly, from the equations (11), (12) and (13) we obtain $$R1 = \frac{1}{4}\left\{1 + \alpha 1^2 + 2\alpha 1\cos\frac{2\pi}{\lambda 1} T(n11 - n12)\right\} \quad (17)$$

$$R2 = \frac{1}{4}\left\{1 + \alpha 2^2 + 2\alpha 2\cos\frac{2\pi}{\lambda 2} T(n21 - n22)\right\} \quad (18)$$

$$R3 = \frac{1}{4}\left\{1 + \alpha 3^2 + 2\alpha 3\cos\frac{2\pi}{\lambda 3} T(n31 - n32)\right\} \quad (19)$$

The values R1, R2, R3, α1, α2, and α3 in the equations (17), (18) and (19) are actual measurements, so that T(n11−n12), etc. can be determined in the same manner as above. Each of R1, R2 and R3 used is the ratio of the photodetector output in the direction of the main refractive index n11 or the like, i.e., the direction AA' in FIG. 3, to the photodetector output in the direction QQ', because the above calculations are based on these directions.

Thus, the retardation values T(n11−n12), etc. of the sample are determined for the respective kinds of light with the wavelengths λ1, λ2 and λ3. The relation between the wavelength and the difference between the two main refractive indexes, i.e. birefringence n1−n2, is then determined in the following manner.

Generally in the visible region, the relation between the refractive index n and the wavelength λ of visible light can be expressed approximately by Cauchy's formula, i.e., by $$n = a + \frac{b}{\lambda^2} + \frac{c}{\lambda^4} \quad (20)$$

where a, b and c are constants dependent on the substance concerned. Considering that these values differ in the respective directions of major axis and minor axis of the indicatrix as a1, a2; b1, b2; and c1, c2, we obtain $$n1(\lambda) = a1 + \frac{b1}{\lambda^2} + \frac{c1}{\lambda^4}$$

$$n2(\lambda) = a2 + \frac{b2}{\lambda^2} + \frac{c2}{\lambda^4}$$

Assuming that the birefringence is Δn(λ), this value can be expressed as $$\begin{aligned}\Delta n(\lambda) &= n2(\lambda) - n1(\lambda) \\ &= a2 - a1 + (b2 - b1)\frac{1}{\lambda^2} + (c2 - c1)\frac{1}{\lambda^4} \\ &= p + \frac{q}{\lambda^2} + \frac{r}{\lambda^4}\end{aligned} \quad (22)$$

where p, q and Y are coefficients relating to the wavelength dependence of the birefringence.

Suppose the thickness of the sample is T. Since Rt(λ)=Δn(λ)T, we obtain $$Rt(\lambda) = T\left(p + \frac{q}{\lambda^2} + \frac{r}{\lambda^4}\right) \quad (23)$$

The method described above therefore gives the retardation values Rt(λ1), Rt(λ2) and Rt(λ3) for the three wavelengths. Since T is known, the values p, q and λ can be obtained by solving simultaneous linear equations with three unknowns. Consequently, a dispersion curve of birefringence can be obtained, from which the birefringence value for an opticional wavelength in the visible region can be known. It is of course easy to determine a dispersion curve from the measurements at four different wavelengths.

Next, examplary results of measurements will be given. The birefringence of six samples were determined using three wavelengths of $\lambda 1=487.5$ nm, $\lambda=590.0$ nm and $\lambda 3=657.3$ nm, and p, q and Y were calculated from the equation (23). Table 2 shows the values obtained.

Figure 5:
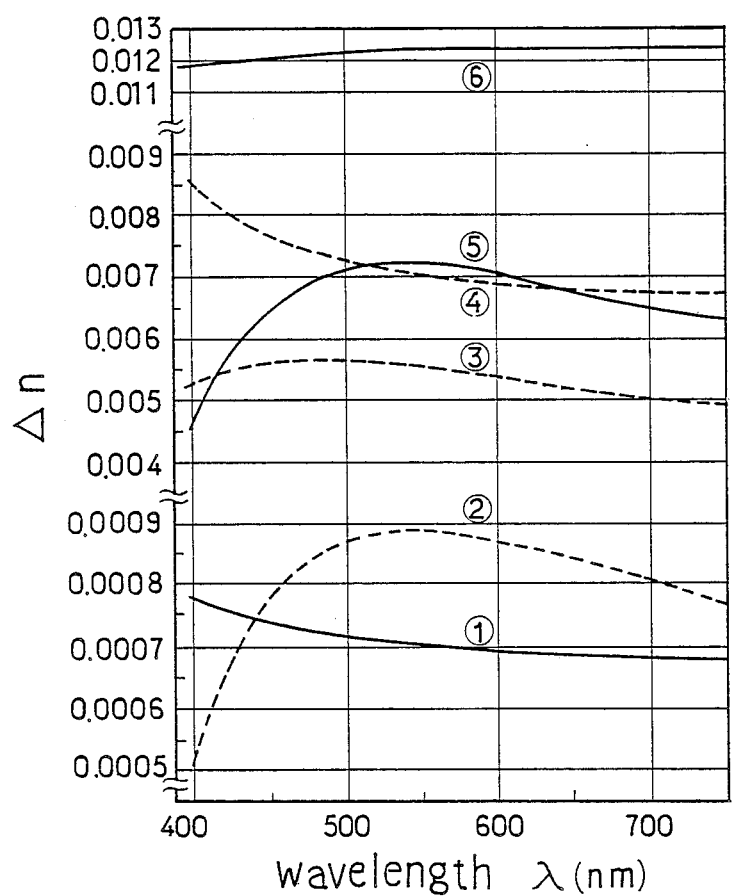
FIG. 5 is a graph showing exemplary results of measurement.

FIG. 5 shows the wavelength dependence of birefringence of the samples as determined with use of the values p, q and $\lambda$ over the wavelength range of 400 nm to 750 nm. The six samples used were films of FEP (fluorinated polymer), PS (polystyrene), PET (polyethylene terephthalate) or PP (polypropylene). FIG. 5 reveals that the wavelength dependence of double refraction differs with different samples. In this way, it is possible according to the present invention to determine the dispersion of birefringence and the value of birefringence at an optional wavelength in the visible region.

wavelength so as to exhibit substantially the same refractive index, selecting a pair of values closest to each other respectively from a multiplicity of retardation values calculated from the result of the determination for the light of one of the wavelengths and from a multiplicity of retardation values calculated from the result of the determination for the light of the other wavelength, and calculating the birefringence from the selected values.

2. A method as defined in claim 1 wherein the directions of polarizaiton of the polarizer and the analyzer are in parallel to each other.

3. A method for measuring the birefringence of a sample characterized by inserting the sample between a polarizer and an analyzer in combination therewith, the polarizer and the analyzer having their directions of polarization fixed at a specified angle with each other, determining the relationship between the angle of rotation and the intensity of light transmitted through the polarizer, the sample and the analyzer when the polarizer and the analyzer are rotated ralative to the sample, for at least three kinds of light, selecting a set of values

TABLE 2

| No. | Sample Kind | Thickness ($\mu$m) | Birefringence $\Delta$n measured (nm) | | | Coefficient of Eq. (22) | | |
|---|---|---|---|---|---|---|---|---|
| | | | $\lambda = 487.5$ nm | $\lambda = 590.0$ nm | $\lambda = 657.3$ nm | P | q (m$^2$) | r (m$^4$) |
| 1 | FEP | 148 | 0.00072 | 0.00069 | 0.00068 | 0.00066 | $3.0195 \times 10^{-18}$ | $2.2183 \times 10^{-30}$ |
| 2 | PET | 58 | 0.00086 | 0.00088 | 0.00083 | 0.00036 | $3.1266 \times 10^{-16}$ | $-4.5981 \times 10^{-29}$ |
| 3 | PS | 60 | 0.00566 | 0.00541 | 0.00518 | 0.00351 | $9.7996 \times 10^{-16}$ | $1.1178 \times 10^{-28}$ |
| 4 | PET | 15 | 0.00733 | 0.00690 | 0.00680 | 0.00688 | $-2.0563 \times 10^{-16}$ | $7.4179 \times 10^{-29}$ |
| 5 | PET | 44 | 0.00703 | 0.00712 | 0.00680 | 0.00328 | $2.2894 \times 10^{-15}$ | $-3.3223 \times 10^{-28}$ |
| 6 | PP | 59 | 0.01221 | 0.01235 | 0.01238 | 0.01237 | $5.4630 \times 10^{-17}$ | $-2.2239 \times 10^{-29}$ | we claim:

1. A method for measuring the birefringence of a sample characterized by inserting the sample between a polarizer and an analyzer in combination therewith, the polarizer and the analyzer having their directions of polarization fixed at a specified angle with each other, determining the relationship between the angle of rotation and the intensity of light transmitted through the polarizer, the sample and the analyzer when the polarizer and the analyzer are rotated relative to the sample, for two kinds of light which are close to each other in closest to one another from a multiplicity of retardation values calculated from the result of the determination for the light of each wavelength, determining a retardation value for each wavelength, and calculating the birefringence for each wavelength from the resulting value.

4. A method as defined in claim 3 wherein the directions of polarization of the polarizer and the analyzer are in parallel to each other.

* * * * *